US008501700B2

(12) United States Patent
Nagasawa

(10) Patent No.: US 8,501,700 B2
(45) Date of Patent: Aug. 6, 2013

(54) METHOD TO ENHANCE DELIVERY OF GLUTATHIONE AND ATP LEVELS IN CELLS

(75) Inventor: Herbert T. Nagasawa, Irvine, CA (US)

(73) Assignee: Max International LLC, Salt Lake City, UT (US)

( * ) Notice: Subject to any disclaimer, the term of this patent is extended or adjusted under 35 U.S.C. 154(b) by 836 days.

(21) Appl. No.: 12/182,354

(22) Filed: Jul. 30, 2008

(65) Prior Publication Data

US 2009/0042822 A1     Feb. 12, 2009

Related U.S. Application Data

(63) Continuation of application No. 10/990,933, filed on Nov. 17, 2004, now abandoned.

(51) Int. Cl.
*A61K 31/70* (2006.01)

(52) U.S. Cl.
USPC ............................................................ 514/27

(58) Field of Classification Search
None
See application file for complete search history.

(56) References Cited

U.S. PATENT DOCUMENTS

| | | | |
|---|---|---|---|
| 4,335,210 A | 6/1982 | Meister et al. | |
| 4,605,644 A | 8/1986 | Foker | |
| 4,719,201 A | 1/1988 | Foker | |
| 4,868,114 A | 9/1989 | Nagasawa et al. | |
| 5,631,234 A | 5/1997 | Ozawa et al. | |
| 6,218,366 B1 | 4/2001 | St. Cyr et al. | |
| 6,534,480 B2 | 3/2003 | Cyr et al. | |
| 2006/0105972 A1 | 5/2006 | Nagasawa | |

FOREIGN PATENT DOCUMENTS

| | | |
|---|---|---|
| EP | 0257992 A2 | 3/1988 |
| WO | WO-2006055597 A1 | 5/2006 |

OTHER PUBLICATIONS

"U.S. Appl. No. 10/990,933, Non-Final Office Action mailed Aug. 21, 2007", 7 p.
"U.S. Appl. No. 10/990,933, Response filed Dec. 6, 2007 to Non-Final Office Action mailed Aug. 21, 2007", 8 p.
"U.S. Appl. No. 10/990,933 Final Office Action mailed Jan. 31, 2008", 6 p.
"International Application No. PCT/US2005/041458, International Search Report mailed Mar. 24, 2005", 5 p.
Bogner, R., et al., "Substituierte Thiazolidine durch Reaktion von L-Cystein mit Monosacchariden", *Liebigs Ann. Chem.*, 738, (1970), 68-78.
Caroll, M. P., et al., "Efficacy of radioprotective agents in preventing small and large bowel radiation injury", *Dis Colon Rectum.*, 38 (7), (Jul. 1995), 716-22.
Jaeschke, H., "Glutathione Disulfide as Index of Oxidant Stress in Rat Liver During Hypoxia", *Am. J. Physiol. Gastrointest. Liver Physiol.*, 258, Abstract Only, Retrieved from the Internet: <URL: http://www.ncbi.nlm.nih.gov/sites/entrez>, (1990), 1 p.
Klassen, Curtis D., et al., "Role of sulfhydryls in the hepatotoxicity of organic and metallic compounds", *Fundamental and Applied Toxicology*, 5, (1985), 806-815.
Lucas, A. M., et al., "Ribose cysteine protects against acetaminophen-induced hepatic and renal toxicity", *Toxicol Pathol.*, 28(5), (Sep.-Oct. 2000), 697-704.
Nagasawa, H. T., et al., "2-Substituted thiazolidine-4(R)-carboxylic acids as prodrugs of L-cysteine. Protection of mice against acetaminophen hepatotoxicity", *J Med Chem.*, 27(5), (1984), 591-596.
Roberts, J. C., et al., "Chemoprotection against cyclophosphamide-induced urotoxicity: ribose-cysteine", *Anticancer Research*, 14(2A), (Mar.-Apr. 1994), 383-7.
Roberts, J. C, et al., "Prodrugs of L-cysteine as protective agents against acetaminophen-induced hepatotoxicity. 2-(Polyhydroxyalkyl)- and 2-(polyacetoxyalkyl)thiazolidine-4(R)-carboxylic acids", *Journal of Medicinal Chemistry*, 20(10), (Oct. 10, 1987), 1891-1896.
Roberts, J. C., "Time course for the elevation of glutathione in numerous organs of L1210-bearing CDF1 mice given the L-cysteine prodrug, RibCys", *Toxicology Letters*, 59(1-3), (Dec. 1991), 245-51.
Rowe, J. K., et al., "Protective effect of RibCys following high-dose irradiation of the rectosigmoid", *Dis Colon Rectum.*, 36(7), (Jul. 1993), 681-8.
Arfsten, D.P., et al, Impact of 30-day oral dosing with N-acetyl-L-Cysteine 5 on Sprague-Dawley rat physiology, Int J Toxicol. Jul.-Aug. 2004;23(4):239-47.
Baker, D.H., Comparative species utilization and toxicity of sulfur amino acids, J Nutr. Jun. 2006;136(6 Suppl):1670S-1675S.
Ball, R.O., et al, The in vivo sparing of methionine by Cysteine in sulfur amino acid requirements in animal models and adult humans, J Nutr. Jun. 2006;136(6 Suppl):1682S-1693S.
Brosnan, J. and Brosnan, M., The Sulfur-Containing Amino Acids: An Overview, J Nutr. Jun. 2006;136(6 Suppl):1636S-1640S.
Cerny, C. and Davidek, T., Formation of Aroma Compounds from Ribose and Cysteine during the Maillard Reaction, J Agric Food Chem. Apr. 23, 2003;51(9):2714-21.
Cooper, A.J.L., et al., On the Chemistry and Biochemistry of 3-Mercaptopyruvic Acid, the α-Keto Acid Analog of Cysteine, J Biol Chem. Jan. 25, 1982;257(2):816-26.
Fukagawa, N., Sparing of Methionine requirements: Evaluation of Human Data Takes Sulfur Amino Acids beyond Protein, J Nutr. Jun. 2006;136(6 Suppl):1676S-1681S.
Garlick, P.J., The nature of human hazards associated with excessive intake of amino acids, J Nutr. Jun. 2004;134 (6 Suppl):1633S-1639S; discussion 1664S-1666S, 1667S-1672S.
Griffiths, J.C., et al., Sub-chronic (13-week) oral toxicity study with D-Ribose in Wistar rats, Food Chem Toxicol. Jan. 2007;45(1):144-52.
Griffiths, J.C., et al., Lack of oral embryotoxicity/teratogenicity with D-Ribose in Wistar rats, Food Chem Toxicol. Mar. 2007;45(3):388-95.
Gross, C.L., et al., Biochemical manipulation of intracellular glutathione levels influences cytotoxicity to isolated human lymphocytes by sulfur mustard, Cell Biol Toxicol. Jul.-Sep. 1993;9(3):259-67. doi:10.1007/BF00755604. PMID 8299004.—Abstract Only.

(Continued)

*Primary Examiner* — Elli Peselev

(74) *Attorney, Agent, or Firm* — Pepper Hamilton LLP

(57) ABSTRACT

A therapeutic method is provided comprising treating a mammal subject to hypoxia with an amount of 2(R,S)-D-ribo-(1', 2',3',4'-tetrahydroxybutyl)thiazolidine-4(R)-carboxylic acid (RibCys) or a pharmaceutically acceptable salt thereof effective to both maintain, restore or increase both the ATP levels and the glutathione (GSH) levels in said tissue.

17 Claims, 2 Drawing Sheets

(56) References Cited

OTHER PUBLICATIONS

Gross, M. and Zollner, N., Serum levels of glucose, insulin, and C-peptide during long term D-Ribose administration in man, Klin Wochenschr. Jan. 4, 1991;69(1):31-6.

Gross, M., et al., Metabolism of D-ribose administered continuously to healthy persons and to patients with myoadenylate deaminanse deficiency, Klin Wochenschr. Dec. 4, 1989;67(23):1205-13.

Harper, A.E., et al, Effects of Ingestion of Disproportionate Amounts of Amino Acids, Physiological Reviews, 1970;60(8): 428-558 (see pp. 449 5-452).

Joseph, C.K., Nutritional Supplements: Amino acids and their derivatives, American Journal of Pharmaceutical Education, 2003;66:157-164.

Kitahori, Y.,et al, Lack of carcinogenicity of L-Cysteine monohydrochloride in fischer 344 rats, J. Toxicol. Pathol., 1997;10:83-89.

Klavins, J.V., Effects of administration of excessive amounts of sulphur containing amino acids: L-cystine, Brit. J. Exptl. Pathol., 1963;44:516-519.

Kleinveld, H.A., et al, Failure of N-acetylCysteine to reduce low-density lipoprotein oxidizability in healthy subjects, Eur J. Clin. Pharmacol., 1992;43: 26 639-642.

Kwayer, Thomas, MD: The Role of Glutathione in Cell Defenses with references to Clinical Deficiencies and Treatment. http://www.fda.gov/ohrms/dockets/ac/00/slides/3652s1_05/s1d001.htm.

Lucas, A.M., et al, Ribose Cysteine Protects Against Acetaminophen-Induced Hepatic and Renal Toxicity, Toxicol Pathol. Sep.-Oct. 2000;28(5):697-704.

Lucas Slitt A.M., et al., Effect of Ribose Cysteine Pretreatment on Hepatic and renal Acetaminophen Metabolite Formation and Glutathione Depletion, Basic Clin. Pharmaco. Toxicol., 2005;96:487-494.

Nagasawa, H.T., et al., Epimerization at C-2 of 2-substituted 5 thiazolidine-4-carboxylic acids, J. Heterocyclic Chem., 1981;18:1047-1051.

Olney, J.W., et al., Cytotoxic effects of acidic and sulphur containing amino acids on the infant mouse central nervous system, Exp. Brain. Res., 1971;14:61-76.

Pompella, A., et al., The changing faces of glutathione, a cellular protagonist, Biochem Pharmacol., Oct. 15, 2003;66(8):1499-503.. doi:10.1016/S0006-2952(03)00504-5. PMID 14555227. http://linkinghub.elsevier.com/retrieve/pii/S0006295203005045.—Abstract Only.

Roberts, J.C. and Francetic, D.J., Mechanisms of Chemoprotection by D-Ribose-L-Cysteine, A Thiazolidine Prodrug of L-Cysteine, Med. Chem. Res., 1991a;1:213-219.

Roberts, J.C. and Francetic, D.J., Time course for the elevation of glutathione in numerous organs of L1210-bearing CDCF1 mice given the L-cysteine prodrug, RibCys, Toxicology Letters, 1991b;59:245-251.

Sauberlich, H. E., Studies on the toxicity and antagonism of amino acids for weanling rats, J. Nutr., 1961;75:61-72.

Sawamoto, O., et al., Four-Week Intravenous Repeated Dose Toxicity Study of L-Cysteine in Male Rats, J. Toxicol. Sci., 2003;28(2):95-107.

Stipanuk, M.H., et al., Mammalian Cysteine metabolism: new insights into regulation of Cysteine metabolism, J. Nutr., 2006;136:1652S-1659S.

Sumioka, I., et al, Acetaminophen-Induced Hepatotoxicity: Still an Important Issue, Yonago Acta Medica, 2004;47: 17-28.

Tribble, D.L., et al, HyperCysteinemia and delayed sulfur excretion in cirrhotics after oral Cysteine loads, Am. J. Clin. Nutr., 1989;50:1401-22 1406.

Van Boekel, M.A.J.S., Formation of flavour compounds in the Maillard reaction, Biotechnology Advances, 2006 24: 230-233.

Van De Poll, M., et al, Adequate Range for Sulfur-Containing amino Acids and Biomarkers for Their Excess: Lessons from Enteral and Parenteral Nutrition, J. 29 Nutr., 2006;136:1694S-1700S.

Vina, J., et al, The effect of Cysteine oxidation on isolated hepatocytes, Biochem. J., 1983;212:39-44.

METHOD TO ENHANCE DELIVERY OF GLUTATHIONE AND ATP LEVELS IN CELLS

CROSS-REFERENCE TO RELATED APPLICATIONS

This application is a continuation of U.S. patent application Ser. No. 10/990,933, filed Nov. 17, 2004, now abandoned, which is hereby incorporated herein by reference.

BACKGROUND OF THE INVENTION

The protective mechanisms of mammalian cells against exogeneous and endogenous stressors that generate harmful free radicals employ the antioxidant co-enzyme, glutathione (GSH). GSH is important in maintaining the structural integrity of cell and organelle membranes and in the synthesis of microtubules and macromolecules. See C. D. Klassen et al. *Fundamental and Applied Toxicology,* 5, 806 (1985). Stimulation of GSH synthesis in rat renal epithelial cells and stomach cells has been found to protect the cells from the toxic effects of cyclophosphamide and serotonin, respectively. Conversely, inhibition of glutathione synthesis and glutathione depletion has been found to have the following effects: (a) decreased cell viability, (b) increased sensitivity of cells to the effects or irradiation, (c) increased sensitivity of tumor cells to peroxide cytolysis, (d) decreased synthesis of prostaglandin E and leukotriene C and (e) selective destruction of trypanosomes in mice.

Biosynthesis of glutathione (GSH) involves two sequential reactions that utilize ATP and that are catalyzed by the enzymes γ-glutamylcysteine synthetase and glutathione synthetase (GSH-synthetase) using the three precursor amino acids L-glutamic acid, L-cysteine, and glycine, as shown in FIG. 1.

All substrate-level reactants occur at near enzyme-saturating concentrations in vivo with the exception of L-cysteine, whose cellular concentration is exceedingly low. Therefore, the first reaction in which L-cysteine is required, i.e., the synthesis of γ-L-glutamyl-L-cysteine, is the rate-limiting step of glutathione biosynthesis. Thus, the availability of intracellular L-cysteine is a critical factor in the overall biosynthesis of GSH, are sufficient stores of ATP.

In the synthesis of ATP via the nucleotide salvage pathway, the nucleotide precursors that may be present in the tissue are converted to AMP and further phosphorylated to ATP. Adenosine is directly phosphorylated to AMP, while xanthine and inosine are first ribosylated by 5-phosphoribosyl-1-pyrophosphate (PRPP) and then converted to AMP.

Ribose is found in the normal diet only in very low amounts, and is synthesized within the body by the pentose phosphate pathway. In the de novo synthetic pathway, ribose is phosphorylated to PRPP, and condensed with adenine to form the intermediate adenosine monophosphate (AMP). AMP is further phosphorylated via high energy bonds to form adenosine diphosphate (ADP) and ATP.

During energy consumption, ATP loses one high energy bond to form ADP, which can be hydrolyzed to AMP. AMP and its metabolites adenine, inosine and hypoxanthine are freely diffusible from the muscle cell and may not be available for resynthesis to ATP via the salvage pathway.

The availability of PRPP appears to control the activity of both the salvage and de novo pathways, as well as the direct conversion of adenine to ATP. Production of PRPP from glucose via the pentose phosphate pathway appears to be limited by the enzyme glucose-6-phosphate dehydrogenase (G6PDH). Glucose is converted by enzymes such as G6PDH to ribose-5-phosphate and further phosphorylated to PRPP, which augments the de novo and salvage pathways, as well as the utilization of adenine.

Many conditions produce hypoxia. Such conditions include acute or chronic ischemia when blood flow to the tissue is reduced due to coronary artery disease or peripheral vascular disease where the artery is partially blocked by atherosclerotic plaques. In U.S. Pat. No. 4,719,201, it is disclosed that when ATP is hydrolyzed to AMP in cardiac muscle during ischemia, the AMP is further metabolized to adenosine, inosine and hypoxanthine, which are lost from the cell upon reperfusion. In the absence of AMP, rephosphorylation to ADP and ATP cannot take place. Since the precursors were washed from the cell, the nucleotide salvage pathway is not available to replenish ATP levels. It is disclosed that when ribose is administered via intravenous perfusion into a heart recovering from ischemia, recovery of ATP levels is enhanced.

Transient hypoxia frequency occurs in individuals undergoing anesthesia and/or surgical procedures in which blood flow to a tissue is temporarily interrupted. Peripheral vascular disease can be mimicked in intermittent claudication where temporary arterial spasm causes similar symptoms. Finally, persons undergoing intense physical exercise or encountering high altitudes may become hypoxic. U.S. Pat. No. 6,218,366 discloses that tolerance to hypoxia can be increased by the administration of ribose prior to the hypoxic event.

Hypoxia or ischemia can also deplete GSH. For example, strenuous aerobic exercise can also deplete antioxidants from the skeletal muscles, and sometimes also from the other organs. Exercise increases the body's oxidative burden by calling on the tissues to generate more energy. Making more ATP requires using more oxygen, and this in turn results in greater production of oxygen free radicals. Studies in humans and animals indicate GSH is depleted by exercise, and that for the habitual exerciser supplementation with GSH precursors may be effective in maintaining performance levels. See L. L. Ji, *Free Rad. Biol. Med.,* 18, 1079 (1995).

Tissue injury, as from burns, ischemia and reperfusion, surgery, septic shock, or trauma can also deplete tissue GSH. See, e.g., K. Yagi, Lipid Peroxides in Biology and Medicine, Academic Press, N.Y. (1982) at pages 223-242; A. Blaustein et al., *Circulation,* 80, 1449 (1989); H. B. Demopoulos, Pathology of Oxygen, A. P. Autor, ed., Academic Press, N.Y. (1982) at pages 127-128; J. Vina et al., *Brit. J. Nutr.,* 68, 421 (1992); C. D. Spies et al., *Crit. Care Med.,* 22, 1738 (1994); B. M. Lomaestro et al., *Annals. Pharmacother.,* 29, 1263 (1995) and P. M. Kidd, *Alt. Med. Res.,* 2, 155 (1992).

It has been hypothesized that delivery of L-cysteine to mammalian cells can elevate GSH levels by supplying this biochemical GSH precursor to the cell. However, cysteine itself is neurotoxic when administered to mammals, and is rapidly degraded. In previous studies, it was shown that N-acetyl-L-cysteine, L-2-oxothiazolidine-4-carboxylate, as well as 2(R,S)-n-propyl-, 2(R,S)-n-pentyl and 2(R,S)-methyl-thiazolidine-4R-carboxylate can protect mice from heptatotoxic dosages of acetaminophen. See H. T. Nagasawa et al., *J. Med. Chem.,* 27, 591 (1984) and A. Meister et al., U.S. Pat. No. 4,335,210. L-2-Oxothiazolidine-4-carboxylate is converted to L-cysteine via the enzyme 5-oxo-L-prolinase. As depicted in FIG. 2, compounds of formula 1, e.g., wherein $R=CH_3$, function as prodrug forms of L-cysteine (2), liberating this sulfhydryl amino aciuc by nonenzymatic ring opening and hydrolysis. However, the dissociation to yield L-cysteine necessarily releases an equimolar amount of the aldehyde (3), RCHO. In prodrugs in which R is an aromatic or an alkyl residue, the potential for toxic effects is present.

U.S. Pat. No. 4,868,114 discloses a method comprising stimulating the biosynthesis of glutathione in mammalian cells by contacting the cells with an effective amount of a compound of the formula (1):

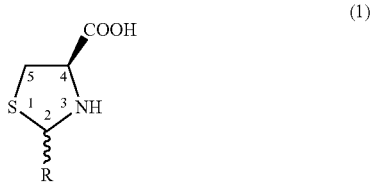

wherein R is a $(CHOH)_nCH_2OH$ and wherein n is 1-5. The compound wherein n is 3 is 2(R,S)-D-ribo-(1',2',3',4'-tetrahydroxybutyl)thiazolidone-4(R)-carboxylic acid (Ribose-Cysteine, RibCys). Following in vivo administration, RibCys releases cysteine by non-enzymatic hydrolysis. RibCys has been demonstrated to be effective to protect against acetaminophen-induced hepatic and renal toxicity. A. M. Lucus, *Toxicol. Pathol.*, 28, 697 (2000). RibCys can also protect the large and small bowel against radiation injury. See M. P. Caroll et al., *Dis. Colon Rectum*, 38, 716 (1995). These protective effects are believed to be due to the stimulation of GSH biosynthesis, which elevates intracellular GSH. However, a need exists for methods to restore or maintain intracellular GSH stores in mammalian tissues subjected to hypoxic conditions in which the ATP stores necessary to drive the biosynthesis of GSH and its precursors are depleted.

SUMMARY OF THE INVENTION

The present invention provides a method to treat a mammal threatened by, or afflicted with a hypoxic condition (hypoxia) comprising administering an effective amount of a compound of formula (Ia):

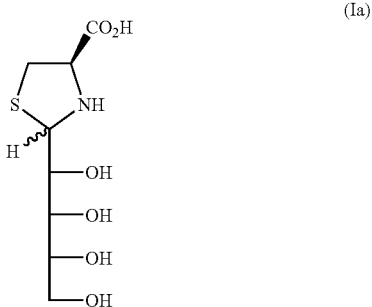 [SMILES: O=C(O)[C@@H]1CSC(C(O)C(O)C(O)CO)N1]

(RibCys) or a pharmaceutically acceptable salt thereof, effective to counteract the effects of said hypoxia in the tissue(s) of said mammal. Although depressed glutathione levels have been implicated in a number of hypoxic conditions, as discussed above, the use of RibCys or its salts to prevent, counteract or otherwise treat such conditions has not been reported. It is believed that simply administering a GSH precursor such as cysteine will not be as effective in many instances of hypoxia, when the depletion of ATP stores contributes to inhibition to the biosynthesis of GSH. As well as functioning as a prodrug for cysteine, administration of effective amounts of RibCys can deliver amounts of ribose to ATP-depleted tissues that stimulate the in vivo synthesis of ATP and that also can stimulate the synthesis of NADPH (nicotinamide adenine dinucleotide phosphate, reduced). This coenzyme supplies the electrons to glutathione reductase, which in turn recycles oxidized GSH via GSSG, to free GSH, which resumes its protective role as a cofactor for antioxidant enzymes in the cell. Optionally, compound (Ia) can be administered with an additional amount of free ribose. Preferably, administration will be by oral administration, particularly in prophylactic or pre-loading situations, but parenteral administration, as by injection or infusion, may be necessary in some situations.

DETAILED DESCRIPTION OF THE INVENTION

Figure 1:
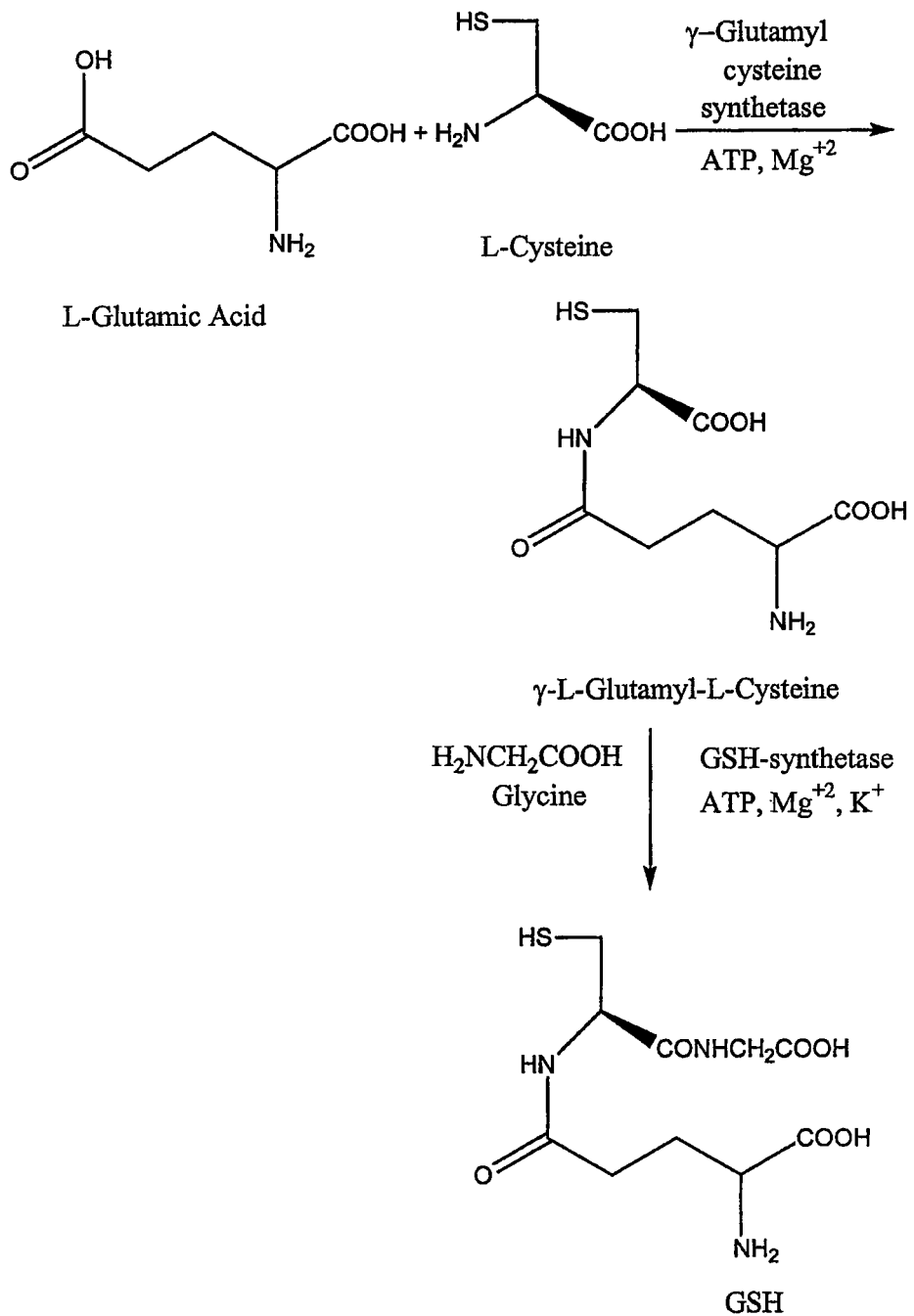
FIG. 1 depicts the metabolic synthesis of glutathione (GSH) from L-glutanic acid.
Figure 2:
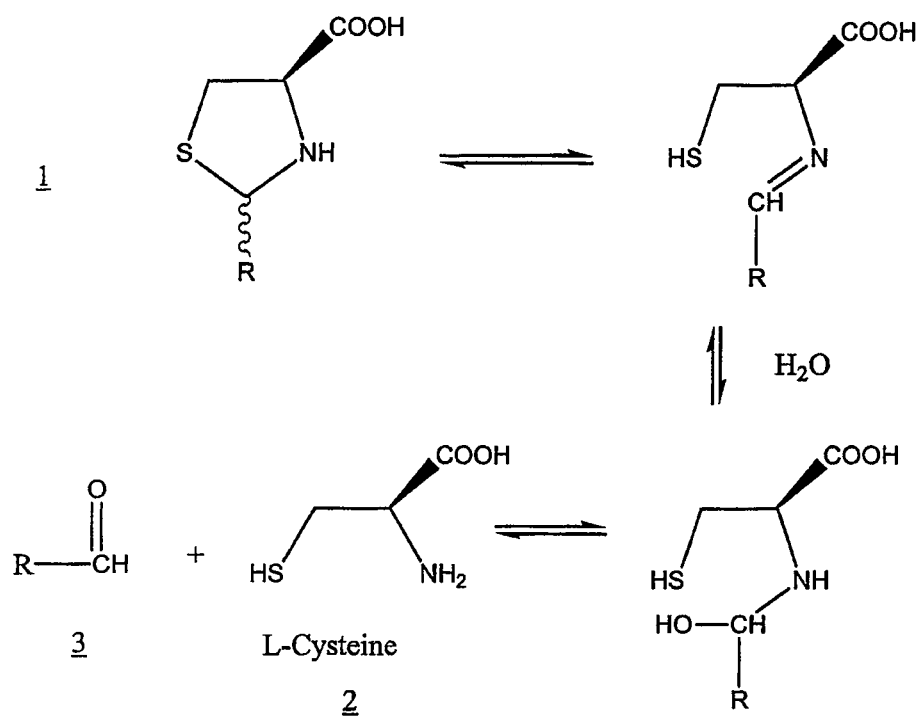
FIG. 2 depicts the in vivo dissociation of a compound of formula I to yield cysteine and an aldehyde.

As used herein, the term RibCys refers to 2(R,S)-D-ribo-(1',2',3',4'-tetrahydroxybutyl) thiazolidine-4(R)-carboxylic acid, as well as the 2R or 2S enantiomers of (Ia), and its pharmaceutically acceptable salts. Such salts include alkali metal salts of the carboxylic acid moiety as well as stable acid addition salts of the NH moiety, including salts of both inorganic and organic acids, such as citrate, malate, gluconate, glutamate, hydrochloride, hydrosulfate and the like.

As used herein, the term "hypoxia" or "hypoxic condition" is defined to mean a condition in which oxygen in one or more tissues of a mammal is lowered below physiologic levels, e.g., to a less than optimal level. Hypoxia also includes conditions in which oxygen levels are lowered in tissues due to stress such as aerobic exercise, physical weight pressure, anesthesia, surgery, anemia, acute respiratory distress syndrome, chronic illness, chronic fatigue syndrome, trauma, burns, skin ulcers, cachexia due to cancer and other catabolic states and the like. Hypoxia also includes "ischemia" or "ischemic conditions" in which tissues are oxygen-deprived due to reduction in blood flow, as due to constriction in, or blockage of, a blood vessel. Ischemia and/or ischemic conditions include those caused by coronary artery disease, cardiomyopathy, including alcoholic cardiomyopathy, angioplasty, stenting, heart surgery such as bypass surgery or heart repair surgery ("open-heart surgery"), organ transplantation, prolonged weight pressure on tissues (pressure ulcers or bedsores), ischemia-reperfusion injury which can cause damage to transplanted organs or tissue, and the like. The present invention is effective to treat the GSH and ATP depletion due to hypoxia and thus to increase a subject's energy level strength and well-being, even though the underlying cause of the hypoxic condition, such as viral or bacterial infection, exposure to bacterial or other toxins, low red-cell counts, aging, cancer or continued exercise, is not affected.

The term "treating" or "treatment" as used herein includes the effects of RibCys administration to both healthy and patients afflicted with chronic or acute illness and includes inducing protective affects as well as decreasing at least one symptom of a past or ongoing hypoxic condition.

Effective doses of RibCys will vary dependent upon the condition, age and weight of the patient to be treated, the condition to be treated and the mode of administration. Both cysteine, as released in vivo from RibCys in animal models, and ribose, as administered directly to human subjects, have been found to be essentially non-toxic over wide dosage ranges. For example, ribose has been reported to increase exercise capacity in healthy human subjects when taken orally at dosages of 8-10 g per day by an adult. See U.S. Pat. No. 6,534,480. RibCys administered to mice at 8 mmol/kg i.p., increased glutathione levels in numerous organs, including heart (1.5×) and muscle tissue (2.5×). See, J. C. Roberts, *Toxicol. Lett.*, 59, 245 (1991). Likewise, RibCys at 8 mmol/kg has been found to deliver effective protective amounts of cysteine to mice exposed to cyclophosphamide. This dose can deliver about 70-80 g of ribose and about 60-70 g of cysteine to an adult human. See J. C. Roberts, *Anticancer Res.*, 14, 383 (1994). Doses of 2 g/kg RibCys were reported to protect mice against acetaminophen hepatic and renal toxicity by A. M. Lucas et al., *Toxicol. Pathol.*, 20, 697 (2000). Doses of 1 g/kg RibCys were reported to protect mice against irradiation-induced bowel injury (see J. K. Rowe et al., *Dis. Colon Rectum*, 36, 681 (1993). J. E. Fuher (U.S. Pat. No. 4,719,201) reported that doses of ribose of about 3 g/day for at least 5 days effectively restored and maintained ATP levels in dogs subjected to ischemia (heart attack model), doses that delivered about 550-700 mg/kg of ribose to an 30 kg dog.

In clinical practice, these compounds, and the pharmaceutically acceptable salts thereof, can be administered in the form of a pharmaceutical unit dosage form comprising the active ingredient in combination with a pharmaceutically acceptable carrier, which can be a solid, semi-solid, or liquid diluent. A unit dosage of the compound can also be administered without a carrier material. Examples of pharmaceutical preparations include, but are not limited to, tablets, powders, capsules, aqueous solutions, suspensions including concentrates, liposomes, and other slow-releasing formulations, as well as transdermal delivery forms. Typically, the unit dosage form includes about 0.001-99% of the active substance.

The compounds can be delivered by any suitable means, e.g., topically, orally, parenterally. Preferably, the delivery form is liquid or a solid such as a powder that can be stirred into an ingestible liquid. Standard pharmaceutical carriers for topical, oral, or parenteral compositions may be used, many of which are described in *Remington's Pharmaceutical Sciences*, Mack Publishing Co., Easton, Pa.

For example, for oral administration, suitable pharmaceutical carriers or diluents can include mannitol, lactose, starch, magnesium stearate, talcum, glucose, and magnesium carbonate. Oral compositions can be in the form of tablets, capsules, powders, solutions, suspensions, sustained release formulations, and the like. A typical tablet or capsule can contain 40-99% lactose, 1-2% magnesium stearate, and 10-20% cornstarch, along with the active substance (preferably about 0.001-20%). An aqueous solution can contain up to the saturation level of RibCys or its salt, preferably with an amount of ribose added that is effective to prevent or inhibit premature in vitro dissociation.

For parenteral administration, suitable pharmaceutical carriers can include water, saline, dextrose, Hank's solution, Ringer's solution, glycerol, and the like. Parenteral compositions can be in the form of suspensions, solutions, emulsions, and the like. Parenteral administration is usually by injection or infusion which can be subcutaneous, intramuscular, or intravenous.

Example 1

2(R,S)-D-ribo-1',2',3',4'-Tetrahydroxybutylthiazolidine-4(R)-carboxylic Acid (RibCys)

This compound was synthesized using ribose (Rib) as described by R. Bognar et al., *Z. Liebigs Ann. Chem.*, 738, 68 (1970), the disclosure of which is incorporated by reference herein. The product was collected to give 4.71 g (92.2% yield) of pale yellow material, mp 149°-151° C. dec. $[\alpha]_D^{25}$-103.1° (c=0.52, H$_2$O); IR (KBr) v3220 (br, OH, COO$^-$), 1610 cm$^{-1}$ (COO$^-$).

Example 2

Stimulation of Glutathione Biosynthesis in Isolated Rat Hepatocytes by L-Cysteine Prodrugs and Inhibition by Buthionine Sulfoximine (BSO)

Rat hepatocytes were isolated following the methods of P. O. Seglen, *Exper. Cell Res.*, 74, 450 (1972). After final plating, the hepatocytes were maintained in culture for 24 hr prior to use. Only primary cultures were used throughout the studies. The hepatocytes were incubated with cysteine prodrugs NAC and (Ia) for a 4-hr period, and after removal of media by aspiration, the cells were rinsed with cold phosphate-buffered saline and deproteinized with 5% sulfosalicylic acid. Total GSH content (GSH+GSSG) was determined by a modification of the DTNB [5,5'-dithiobis(2-nitrobenzoic acid)]glutathione reductase recycling method of F. Tietze, *Anal. Biochem.*, 27, 502 (1969). The GSH concentration in the sample was quantified by determining the cycling rate (ΔOD at 412 nm/min) of the sample. For the inhibition studies with BSO, the cells were pre-exposed to BSO (0.20 mM) before treatment with the L-cysteine prodrugs.

The results are shown in Table 1, below:

TABLE 1

Increased Glutathione [GSH] Content of Rat Hepatocytes after Incubation with L-Cysteine Prodrugs

| Cysteine Prodrug | Conc. (mM) | [GSH] ± SE (nmol/10$^6$ cells) | [GSH] Rel. to Controls |
|---|---|---|---|
| Control (none) | — | 35.4 ± 0.75 | 1 |
| RibCys (Ia) | 1.0 | 61.2 ± 1.52 | 1.7 |
| N-Acetyl-L-cysteine (NAC) | 2.5 | 45.8 ± 1.27 | 1.3 |

As can be seen from Table 1, RibCys elevated GSH levels about 1.7-fold relative to controls in these hepatocytes. N-Acetyl-L-cysteine (NAC), the drug presently used for the clinical treatment of acetaminophen overdoses, also raised GSH levels by 30% in this system, but required 2.5 times the concentration of the thiazolidine prodrugs for comparable elevation. (See L. F. Prescott et al., *Brit. Med. J.*, 2, 1097 (1979); B. J. Lautenburg et al., *J. Clin. Invest.*, 71, 980 (1983) and G. B. Corcoran et al., *J. Pharmacol. Exp. Ther.*, 232, 864 (1985)).

That GSH biosynthesis was stimulated by liberation of its biochemical precursor, L-cysteine, from the prodrugs, was indicated by experiments conducted in the presence of 0.20 mM buthionine sulfoxime (BSO). O. W. Griffith et al., *J. Biol. Chem.*, 254, 7558 (1979), have demonstrated that BSO is a specific inhibitor of gamma-glutamyl cysteine synthetase, the enzyme responsible for catalyzing the first step in GSH biosynthesis. The data summarized on Table 2, below, demonstrate that GSH levels were decreased by this inhibitor even in the presence of RibCys, thus providing evidence that the increased levels of GSH observed were indeed due to de novo GSH biosynthesis from the L-cysteine provided by the thiazolidine prodrugs.

TABLE 2

Inhibitory Effect of Buthionine Sulfoxime (BSO) on GSH
Elevation Elicited by L-Cysteine Prodrugs in Rat Hepatocytes

| Prodrug (1.0 mM) | BSO (0.2 mM) | [GSH] ± SE (nmol/10$^6$ cells) | [GSH] Rel. to Controls. |
|---|---|---|---|
| None (Control) | − | 35.4 ± 0.78 | 1.0 |
| None | + | 18.4 ± 2.08 | 0.5 |
| RibCys (1a) | + | 16.2 ± 3.60 | 0.5 |
| N-Acetyl-L-cysteine | + | 25.5 ± 1.59 | 0.7 |

Example 3

RibCys Elevates GSH in Heart and Muscle Tissue

As reported by J. C. Roberts et al., *Toxicol. Left.*, 59, 245 (1991), RibCys successfully elevated glutathione (GSH) levels in numerous organs of tumor-bearing CDF1 mice. GSH content was assayed 1, 2, 4, 8 and 16 h after RibCys administration (8 mmol/kg, i.p.); various organs achieved maximal GSH content at different time points. GSH in the liver was elevated 1.5-fold compared to untreated controls at the 16-h time point. Kidney GSH also was maximal at 16 h and achieved 1.6-times control values. GSH in muscle achieved 2.5 times the levels in control animals, while the bladder was elevated 2.1-fold, and the heart 1.8-fold. Other tissues tested (spleen, pancreas, lung) showed a 1.1- to 1.2-fold increase in GSH content. GSH in implanted L1210 tumors was also elevated only 1.2-fold.

Example 4

Recovery of the Working Canine Heart Following Global Myocardial Ischemia

As reported in Examples 1-2 of J. E. Foker (U.S. Pat. No. 4,605,644), dilute solutions of ribose in normal (0.9%) saline were found effective to decrease the ATP recovery time following myocardial ischemia in the canine model. For example, infusion of a normal saline solution which is 80 mM in ribose at a rate of about 1 ml/min for about 24.0 hours afforded an eight-fold decrease in the ATP recovery time. During this treatment period, about 17.0 g of ribose were introduced into the circulatory system; a total dose of about 550-700 mg ribose/kg of body weight. The appropriate dose for the optimal recovery of ATP levels and cardiac function in a given human subject can be readily established via empirical studies including known assays for ATP levels, cardiac function and the like.

Although the studies of the examples of U.S. Pat. No. 4,605,644 were directed at enhancing the energetic recovery following ischemia of the heart with solutions containing free ribose, the present method employing the cysteine/ribose prodrug RibCys is also expected to be applicable to any tissue or organ that has suffered hypoxia, such as an ischemic insult where antioxidant augmentation and ATP recovery would be helpful. These situations include but are not limited to: myocardial infarction, stroke, organ transplant with organ preservation, neonatal support, multi-organ system failures, shock and trauma resulting in compromised circulation, and the like. Often, even uncomplicated general anesthesia can result in some degree of hypoxia and the accompanying invasive medical procedure can lead to the build-up of free radicals in the traumatized tissue. Likewise, aerobic exercise in convalescent or healthy individuals can lead to ATP depletion and the build-up of free radicals from environmental oxidants. Therefore, the present invention provides a method whereby hypoxic tissue can be treated so as to quickly regain and maintain normal ATP levels, both to improve tissue survival and to hasten general bodily recovery.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of increasing ATP and glutathione in a mammal in need thereof comprising administering an effective amount of RibCys or a pharmaceutically acceptable salt thereof to said mammal, wherein said RibCys increases both ATP and glutathione, wherein said RibCys is administered in a unit dosage form comprising 20% (w/w) of RibCys.

2. The method of claim 1, wherein said RibCys is administered in a liquid.

3. The method of claim 2, wherein said liquid further comprises an effective amount of ribose to inhibit premature dissociation of the RibCys.

4. The method of claim 3, wherein said liquid comprises an effective amount of ribose to inhibit premature in vitro dissociation of the RibCys.

5. The method of claim 1, wherein said RibCys is administered orally, parenterally, intravenously, or intraperitoneally.

6. The method of claim 1, wherein said RibCys is administered orally.

7. A method of treating hypoxia in a mammal in need thereof by increasing glutathione and ATP comprising administering an effective amount of RibCys or a pharmaceutically acceptable salt thereof to said mammal, wherein said RibCys increases glutathione and ATP to treat said hypoxia.

8. The method of claim 7, wherein said RibCys is administered orally, parenterally, intravenously, or intraperitoneally.

9. The method of claim 7, wherein said RibCys is administered orally.

10. The method of claim 7, wherein said hypoxia is caused by an ischemia.

11. The method of claim 10, wherein said ischemia is caused by cardiovascular disease, cardiomyopathy, myocardial stunning, peripheral vascular disease, intermittent claudication, tachycardia or ischemia-reperfusion.

12. The method of claim 7, wherein said hypoxia results from aesthesia, physical body weight pressure, septicemia, stroke, surgical procedure, burn, pulmonary dysfunction, physical exertion or chronic illness.

13. The method of claim 7, wherein said RibCys is administered in a unit dosage form comprising 20% (w/w) of RibCys.

14. The method of claim 7, wherein said RibCys is administered in a liquid.

15. The method of claim 14, wherein said liquid further comprises an effective amount of ribose to inhibit premature dissociation of the RibCys.

16. The method of claim 15, wherein said liquid comprises an effective amount of ribose to inhibit premature in vitro dissociation of the RibCys.

17. The method of claim 7, wherein said method consists of administering an effective amount of RibCys or a pharmaceutically acceptable salt thereof to said mammal.

* * * * *

UNITED STATES PATENT AND TRADEMARK OFFICE
CERTIFICATE OF CORRECTION

| | |
|---|---|
| PATENT NO. | : 8,501,700 B2 |
| APPLICATION NO. | : 12/182354 |
| DATED | : August 6, 2013 |
| INVENTOR(S) | : Nagasawa |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 833 days.

Signed and Sealed this
Twenty-first Day of July, 2015

Michelle K. Lee
*Director of the United States Patent and Trademark Office*